US012775012B2

(12) United States Patent
Quon et al.

(10) Patent No.: US 12,775,012 B2
(45) Date of Patent: Oct. 27, 2026

(54) METHODS AND SYSTEMS FOR IMMOBILIZING A BIOLOGICAL SPECIMEN FOR MICROSCOPIC IMAGING

(71) Applicant: Beckman Coulter, Inc., Brea, CA (US)

(72) Inventors: Carol Quon, Genoa, NV (US); Bart J. Wanders, Coto de Caza, CA (US); John Mcdonald, Malibu, CA (US)

(73) Assignee: Beckman Coulter, Inc., Brea, CA (US)

( * ) Notice: Subject to any disclaimer, the term of this patent is extended or adjusted under 35 U.S.C. 154(b) by 747 days.

(21) Appl. No.: 17/615,423

(22) PCT Filed: May 29, 2020

(86) PCT No.: PCT/US2020/035311
§ 371 (c)(1),
(2) Date: Nov. 30, 2021

(87) PCT Pub. No.: WO2020/243564
PCT Pub. Date: Dec. 3, 2020

(65) Prior Publication Data

US 2022/0229050 A1 Jul. 21, 2022

Related U.S. Application Data

(60) Provisional application No. 62/854,763, filed on May 30, 2019.

(51) Int. Cl.
*G01N 33/545* (2006.01)
*G01N 15/14* (2006.01)
(Continued)

(52) U.S. Cl.
CPC ....... *G01N 33/545* (2013.01); *G01N 15/1433* (2024.01); *G01N 15/147* (2013.01); *G01N 2015/1006* (2013.01)

(58) Field of Classification Search
CPC ............. G10N 33/545; G01N 15/1433; G01N 15/147; G01N 2015/1006
(Continued)

(56) References Cited

U.S. PATENT DOCUMENTS 4,790,961 A * 12/1988 Weiss ......................... C07J 9/00
552/544
5,548,661 A * 8/1996 Price ..................... G06T 7/0012
382/129
(Continued)

FOREIGN PATENT DOCUMENTS

| | | |
|---|---|---|
| CN | 114174799 | 3/2022 |
| EP | 3163284 | 5/2017 |

(Continued)

OTHER PUBLICATIONS

"International Application Serial No. PCT/US2020/035311, International Search Report mailed Sep. 23, 2020", 5 pgs.
(Continued)

*Primary Examiner* — Stephen S Hong
*Assistant Examiner* — Tionna M Burke
(74) *Attorney, Agent, or Firm* — Schwegman Lundberg & Woessner, P.A.

(57) ABSTRACT

Embodiments of the present invention generally relate to methods for immobilizing a biological specimen for extended periods of time for image capture. Specific embodiments may be used to support a target specimen in a gel matrix. In some embodiments, the biological specimen may be in liquid form at elevated temperatures, a stain and/or lyse may be added to the biological specimen, and a gelling composition may added. At reduced temperatures, the gelling composition may still the biological specimen to immobilize a biological specimen for extended periods of time for image capture.

17 Claims, 3 Drawing Sheets

(51) Int. Cl.
*G01N 15/1433* (2024.01)
*G01N 15/10* (2006.01)

(58) Field of Classification Search
USPC .......................................................... 382/128
See application file for complete search history.

(56) References Cited

U.S. PATENT DOCUMENTS

| | | | | |
|---|---|---|---|---|
| 2004/0200909 A1* | 10/2004 | McMillan | B01L 7/52 | 241/1 |
| 2012/0219470 A1* | 8/2012 | Smith | G01N 33/545 | 422/566 |
| 2015/0167063 A1* | 6/2015 | Shirai | C12N 15/1096 | 506/9 |

FOREIGN PATENT DOCUMENTS

| | | | | |
|---|---|---|---|---|
| JP | H0739324 A * | 2/1994 | | |
| JP | H11169703 A * | 12/1997 | | |
| WO | WO-9107486 A1 | 5/1991 | | |
| WO | WO-2004096309 A1 * | 11/2004 | | A61F 2/0059 |
| WO | WO-2006003423 A2 | 1/2006 | | |
| WO | WO-2017036483 A1 * | 3/2017 | | |
| WO | WO-2020243564 A1 | 12/2020 | | |

OTHER PUBLICATIONS

"International Application Serial No. PCT/US2020/035311, Written Opinion mailed Sep. 23, 2020", 8 pgs.
Khashei, Sanaz, et al., "Immobilization of Pseudomonas putidaPT in resistant matrices to environmental stresses: a strategy for continuous removal of heavy metals under extreme conditions", Annals of Microbiology, Distam, Milan, IT, vol. 68, No. 12, (Nov. 12, 2018), 931-942.
"International Application Serial No. PCT US2020 035311, International Preliminary Report on Patentability mailed Dec. 9, 2021", 10 pages.
"European Application Serial No. 20746406.6, Communication Pursuant to Article 94(3) EPC mailed Feb. 27, 2024", 6 pgs.
"European Application Serial No. 20746406.6, Response filed Jun. 21, 2024 to Communication Pursuant to Article 94(3) EPC mailed Feb. 27, 2024", 10 pgs.
"European Application Serial No. 20746406.6, Response filed Jul. 6, 2022 to Communication pursuant to Rule 161(1) and 162 EPC mailed Jan. 12, 2022", 13 pgs.
Flood, Peter, "Using hydrogels in microscopy: A tutorial", MICRON, vol. 84, (2016), 7-16.
Sigma, "Agarose Product Information", [online]. Retrieved from the Internet https www.sigmaaldrich.com deepweb assets sigmaaldrich product documents 181 864 a9539pis.pdf?, Aug. 3, 2012, 8 pages.
Velasco, Diego, "Microfluidic Encapsulation of Cells in Polymer Microgels", ISSN 1613-6810, Jun. 11, 2012, 10 pages.

* cited by examiner

METHODS AND SYSTEMS FOR IMMOBILIZING A BIOLOGICAL SPECIMEN FOR MICROSCOPIC IMAGING

CLAIM OF PRIORITY

This patent application is a U.S. National Stage Filing under 35 U.S.C. 371 from International Application No. PCT/US2020/035311, filed on 29 May 2020, and published as WO 2020/243564 on Dec. 3, 2020, which application claims the benefit of priority to U.S. Provisional Application Ser. No. 62/854,763, filed May 30, 2019, which are incorporated herein by reference in their entirety.

FIELD OF THE DISCLOSURE

Embodiments of the present disclosure relate generally to methods and systems for immobilizing a biological specimen for microscopic imaging. More particularly, embodiments of the present disclosure relate to immobilizing a biological specimen in a gel composition for extended image-capture times to enable various microscopic imaging techniques. Non-limiting examples may include flow imaging or wet-mount microscopy.

BACKGROUND

Conventionally, biological specimens are smeared on slides and observed/analyzed under a microscope. In automated operations, a specimen is smeared on a slide and placed on a microscope stage. The slide is automatically manipulated, scanned and orientated at various locations along the stage to capture still images of the specimen. Subsequently, the still images are processed using image processing techniques that characterize and recognize patterns in the sample to detect analytes in the sample.

However, the foregoing automation procedure is time consuming and requires complex machinery. These automated processes are not able to achieve high-throughput applications at least because a slide has to be created for each sample. Additionally, this process generates large amounts of biohazardous solid waste since a glass slide is generated for each sample. Moreover, smearing biological specimens on a slide ruptures or modifies cells from their native state.

In an effort to improve efficiency of imaging specimens, various microscopic imaging techniques have been developed that focus on improved image processing for producing high resolution images. For some image processing approaches, a large number of low-resolution images are taken of the same specimen. For example, several hundred to thousands of low-resolution images are taken by an image-capture device. These low-resolution images are then post-processed into a single high-resolution image. Since a large amount of images are taken of the specimen, the image acquisition time is long and the biological specimen has to be stationary for a prolonged period for good quality images.

Because of extended image-capture times, the aforementioned image processing techniques cannot be used for some microscopic imaging. For example, flow imaging cannot be combined with new image processing technologies due to the limited exposure time of the specimen. Additionally, wet-mount microscopy cannot be combined with image processing technologies because of cell mobility.

Therefore, a need exists for immobilizing a biological specimen for extended periods to enable the use of microscopic imaging techniques that require less time and waste, while producing high-resolution images of the target specimen.

BRIEF SUMMARY

Embodiments of this disclosure thus provide a method for immobilizing a biological specimen for microscopic imaging, comprising: providing a gel composition in a first state, wherein the gel composition is thermally reversible between the first state and a second state at a critical temperature; adding a biological specimen to the gel composition to form an aqueous mixture; optionally adding a reagent to the aqueous mixture; cooling the aqueous mixture below the critical temperature of the gel composition to the second state to form a gel matrix, wherein the biological specimen is immobilized in the gel matrix; and capturing a plurality of images of the biological specimen in the gel matrix. In some cases, the gel composition is a liquid in the first state. In some cases, the reagent is a stain, and the method further comprises adding the stain to the aqueous mixture when the gel composition is in the first state. In some cases, the reagent is a lysing agent, and the od further comprises adding the lysing agent to the aqueous mixture when the gel composition is in the first state. In some cases, the gel hardens to form the gel matrix in the second state below the critical temperature. In some cases, the critical temperature is from about 15° C. to 25° C. In some cases, the biological specimen comprises live cells. In some cases, the gel composition may comprise alginate, carrageenan, beta-carrageenan, agar, agarose, curdlan, pullulan, gellan, furcellaran, beta-carrageenan, beta.-1,3-glucans, gelatin, polyoxyalkylene containing compounds, or any combination thereof, wherein the gel composition forms a transparent gel matrix. In some cases, the gel matrix is applied to a surface of an imaging substrate. In some cases, the gel matrix serves as a support for the analysis of the biological specimen by flow imaging, microscopy or non-imaging plate based assays.

In some embodiments, the present disclosure provides a method for imaging a biological sample in a flow imaging system, comprising: preparing a specimen sample for a flow imaging cytometer, comprising: providing a gel composition in a first state, wherein the gel composition is thermally reversible between the first state and a second state at a critical temperature; adding a biological specimen to the gel composition to form an aqueous mixture; cooling the aqueous mixture below the critical temperature of the gel composition to the second state to form a specimen solution comprising a gel matrix, wherein the biological specimen is immobilized in the gel matrix; flowing the specimen sample through an image capture area of the flow cytometer; and capturing a plurality of images of the specimen sample. In some cases, the flow cytometer captures a plurality of low resolution images of the specimen sample. In some cases, portions of the specimen sample are exposed to the image capture area for at least 5 seconds. In some cases, the gel composition may comprise alginate, carrageenan, beta-carrageenan, agar, agarose, curdlan, pullulan, gellan, furcellaran, beta-carrageenan, beta-1,3-glucans, gelatin, polyoxyalkylene containing compounds, or any combination thereof, wherein the gel composition forms a transparent gel matrix. In some cases, preparing a specimen sample further comprises adding a stain or lyse composition to the aqueous mixture.

In some embodiments, the present disclosure provides a method for imaging a biological sample in a flow imaging system in a wet-mount system comprising: preparing a specimen sample, comprising: providing a gel composition in a first state, wherein the gel composition is thermally reversible between the first state and a second state at a critical temperature; adding a biological specimen to the gel composition to form an aqueous mixture; cooling the aqueous mixture below the critical temperature of the gel composition to the second state to form a specimen solution comprising a gel matrix, wherein the biological specimen is immobilized in the gel matrix; placing a portion of the specimen sample on a microscope slide; and capturing a plurality of images of the specimen sample. In some cases, the plurality of images are low-resolution images, and wherein each of the plurality of images are still images of the immobilized biological specimen in the gel matrix. In some cases, the gel composition may comprise alginate, carrageenan, beta-carrageenan, agar, agarose, curdlan, pullulan, gellan, furcellaran, beta-carrageenan, beta-1,3-glucans, gelatin, polyoxyalkylene containing compounds, or any combination thereof, wherein the gel composition forms a transparent gel matrix. In some cases, preparing a specimen sample further comprises adding an aliquot of stain or lyse composition to the aqueous mixture.

DETAILED DESCRIPTION

Figure 1:
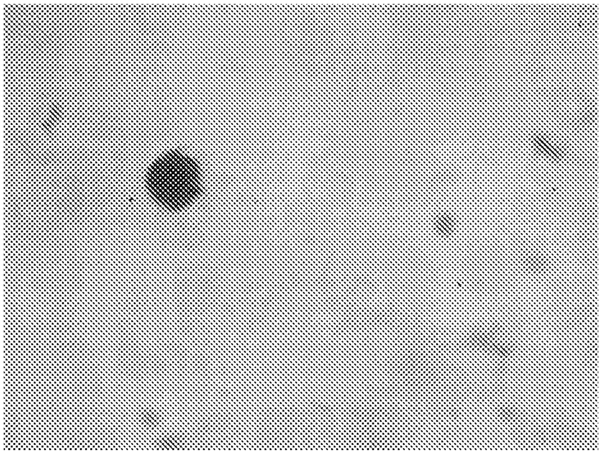
FIG. 1 shows an example of an immobilized basophil in a gel according to one embodiment of the present disclosure.

Embodiments of the present disclosure relate to research, diagnostic and screening assays for biological samples. Specific embodiments of the present disclosure may be used to immobilize biological samples in a gel composition during continuous or periodic analyses by microscopy or imaging methods thereby reducing the compromising effects of: cell motility, cell detachment from a substrate, the effects of Brownian motion, physical disturbance of cell locations or the loss of inter-relationships during sample manipulation. In some embodiments, active components in a biological sample may be immobilized within a gel matrix that is formed below a critical temperature. In some embodiments, the biological samples may include multicellular structures, cells, viruses, proteins, enzymes, nucleic acids such as DNA, and the like. In some embodiments, the biological samples may include intracellular structures and parasites. In some embodiments, the gel compositions are live-cell compatible and are used to immobilize biological specimens for sequential imaging of different optical planes for 3D re-construction or acquisition of images for camera-based microscopy approaches.

As described above, new imaging techniques require extended image-capture times for taking numerous images of biological specimens in a biological sample. For example, flow-imaging cytometry captures images of a sample solution in an image capture area for cells traveling in the flow of a specimen solution and is constantly monitored to perform cell photography. Flow imaging cytometry enables high throughput analysis of samples and provides a means for analysis of samples in their native state. Comparatively, when a sample is smeared on a slide, the cells are ruptured or modified from their native state. For example, when blood is smeared on slide, red blood cells are often ruptured.

However, the exposure time in flow imaging cytometry limits the use of new image processing technologies that require extended image-capture times. For example, flow-imaging cytometry has an exposure time of approximately 1.8 microseconds. In order to take a multitude of low-resolution images, the specimen flowing in the image capture area may need to be exposed for a period for an adequate number of images to be taken. In some cases, the specimen should be exposed for at least 5 seconds or more. In some cases, the specimen should be exposed for at least 8 seconds or more. In some cases, the specimen should be exposed for at least 10 seconds or more. In some cases, the specimen should be exposed from 5 seconds to 30 seconds, e.g., from 6 seconds to 28 seconds, from 8 seconds to 26 seconds, from 10 seconds to 24 seconds, from 12 seconds to 22 seconds, from 14 seconds to 20 seconds, or from 16 seconds to 18 seconds.

The inventors have found that a biological specimen can be immobilized in a gel composition to provide extended image-capture times. Additionally, by utilizing a gel composition, the viscosity of the sample fluid containing the biological specimen can be controlled to slow the flow of a specimen solution in an image capture area of a flow imaging cytometer. For example, the gel composition can form a high viscosity gel containing the biological specimen to slow the flow of the biological specimen (while immobilizing the cells of the biological specimen in the gel) in the flow cytometer to provide an image capture time ranging from 5 seconds to 30 seconds. Specifically, under gelling conditions (e.g., in liquid form at elevated temperatures but in gel form at lower temperatures), the gel composition comprising the biological specimen hardens to form a gel to inhibit or stop Brownian motion of cells in the biological specimen, which conventionally causes image-capture problems in flow cytometry. Advantageously, the extended image-capture times enable flow-imaging devices to take a series of low-resolution images of the still cells in the biological specimen. The series of low-resolution images can be subsequently post-processed to produce a high-resolution image of the specimen in its native state. In some cases, the low-solution images are processed using artificial intelligence to convert the low-resolution images to one or more high-resolution images. The gel composition added to a biological specimen allows for the use of flow imaging with all of its benefits, while being able to use new image processing technologies.

In one embodiment, a method for immobilizing a biological specimen for microscopic imaging comprises: providing a gel composition in a first state, wherein the gel composition is thermally reversible between the first state and a second state at a critical temperature; adding a biological specimen to the gel composition to form an aqueous mixture; optionally adding a reagent to the aqueous mixture; cooling the aqueous mixture below the critical temperature of the gel composition to the second state to form a gel matrix, wherein the biological specimen is immobilized in the gel matrix; and capturing a plurality of images of the biological specimen in the gel matrix.

In some cases, the gel composition provides an inert environment for the biological sample. For example, the gel composition does not chemically interact with the cells of a biological sample. The cells of the biological sample in the gel composition are able to function normally and are encapsulated in the gel matrix. The gel composition forms a hardened solution that inhibits Brownian motion of cells in the biological sample without altering (e.g., breaking) the cells from their native state. The gel composition is used to inhibit or stop natural movement (e.g., Brownian movement and fluidic movement) of the cells so that a plurality images can be captured in the time needed; however, the gel is still soft and pliable for manipulation of the sample. For thermally-reversible gel compositions, at temperatures above the critical temperature of the gel, biological samples can be incorporated while the gel is in liquid form. When the temperature is reduced, for example to room temperature, the gel composition forms a gel and the cells become trapped in the gel matrix. It is possible to administer any necessary or desirable reagents, while the gel is in the liquid phase thus ensuring the cells are able to absorb the necessary agents in the gel matrix. Non-limiting examples including adding a stain or lyse composition to the gel in its liquid phase. After imaging, the temperature of the gel matrix with the trapped cells can be increased to allow the cells to be extracted by transition to the liquid phase. In some aspects, the temperature of the gel is increased in selected regions of the gel thereby permitting micro-selection of cell populations with given characteristics without any adverse effects. In this way, the liquid gel composition containing the biologic specimen can be disposed in an efficient manner.

In some embodiments, the present disclosure provides a method for immobilizing a biological specimen in a gel composition. The gel composition may be thermally reversible. In other words, the gel composition is thermally reversible from a liquid phase at a temperature above its critical temperature to a gel phase at a temperature below its critical temperature, or vice versa. In some cases, the gel composition may be initially provided in liquid fours at a temperature above its critical temperature. A biological specimen can be added to the gel composition to form an aqueous mixture. One or more reagents can be optionally added to the aqueous mixture. For example, a stain or lyse can be added to the aqueous mixture. The temperature of the aqueous mixture can be reduced below the critical temperature of the gel composition to immobilize the biological specimen in a gel matrix. The gel properties can be modified by formulation providing polymers with different transition temperatures suitable for different applications. The gel composition can be used to trap, support, over-layer, or suspend particles, beads, cells, etc., prior to or during manipulation. Upon temperature shift, the gel hardens to transition from a sol liquid form) to a gel providing an immobilized cell/particle in a gel matrix. For example, the gel can undergo positive or passive cooling to form the gel matrix. In some embodiments, the gel composition can have low viscosity at temperatures above room temperature (e.g., the sol-form) and can have a high viscosity at room temperature (e.g., gel-form).

The rapid formation of a gel at the critical temperature immobilizes the biological sample and provides a support matrix for manipulation, analysis or processing of cells. For example, the gel can immobilize live cells to prevent Brownian motion. It is also contemplated that the rapid formation of the gel provides an immobilizing layer on the cells. In this way, the immobilizing layer can also protect the cells when applied on a microscope slide or when compressed with a coverslip. The thermal reversibility of the gel allows these cells to be selectively removed and further processed. Additionally, the gel formation provides a high-viscosity biological specimen, thereby eliminating the need for smearing the biological specimen on a microscope slide.

In some cases, the matrix formed by the gel is a three dimensional structure that provides support for the immobilized biological specimens. The matrix structure serves as a skeleton which maintains the integrity of the gel. The nature of the matrix structure employed for the gel affects the porosity and other characteristics of the network of the matrix. In some embodiments, a gel composition that produces a three dimensional matrix structure with a specific porosity can be provided based on the desired functions of the gel matrix.

Additionally, one or more reagents can be added to the gel composition for biological modification that would impart additional functionalities to the gel composition. In some embodiments, a "reagent" may include any suitable substance used for its chemical or biological activity. Reagents may be in liquid or dried form. Examples of reagents may include reporters (e.g., markers), support reagents such as lysis solutions, stains, buffers, etc. For example, growth factors or signaling molecules can be added to the gel composition to maintain or modify specific cellular phenotypes. In some embodiments, reagents can be added for the purpose of modifying the photophysical and photochemical effects of light illumination on cells or reporter molecules would impart additional functionalities to the gel composition to improve image capture during flow cytometry. For example, in the gel phase or liquid phase, reagents may be added to modify the cells in the biological sample.

The gel composition may be present in the aqueous mixture in a wide range of concentrations, the precise amount depending on the application intended for the gel, on the physical characteristics of the gel, on the gelling properties of the gel forming component used, and other similar factors. In some embodiments, the gel-forming component may be present in very low concentrations, in amounts as low as 1 wt % or less, based on the total weight of aqueous mixture. In some embodiments, the gel-forming component of the aqueous mixture is present in amounts of from about 0.1 wt. % to about 25 wt. %., based on the total weight of the aqueous mixture. In some embodiments, the gel-forming component of the aqueous mixture is present in amounts of from about 0.5 wt. % to about 20 wt. %., based on the total weight of the aqueous mixture. In some embodiments, the gel-forming component of the aqueous mixture is present in amounts of from about 1 wt. % to about 10 wt. %., based on the total weight of the aqueous mixture.

In some embodiments, suitable gel-forming materials may include polysaccharide hydrogels. Non-limiting examples include alginate, carrageenan, agar, curdlan, pullulan, gellan, or any appropriate combination thereof. In some embodiments, a variety of hydrogels based upon thermally reversible polymers (in liquid form at elevated temperatures but in gel form at lower temperatures) can be utilized. Non-limiting examples include natural gel-forming materials such as agarose, agar, furcellaran, beta-carrageenan, beta-1,3-glucans such as curdlan, gelatin, or polyoxyalkylene containing compounds, or any appropriate combinations thereof. In some embodiments, suitable gel-forming materials may include agarose gels because of their low gelling/melting temperature and are especially useful in gel matrix applications involving biologically active materials. Commercially available agar powders may include, for example, Agar A-7002, Agar A-9414, and Agar A-9045 from Sigma Aldrich Co. Ltd. In some cases, preferred agar powders are low melting point agars (e.g., melting point less than about 75° C.).

In some embodiments, an agar powder may be added to deionized water to form an agar solution. The agar solution may comprise from about 0.1 wt. % to about 10 wt. % agar (e.g., from about 0.5 wt. % to about 8 wt. %, from about 0.8 wt. % to about 5 wt. %, or from about 0.9 wt. % to about 2 wt. %). In some embodiments, the agar solution may comprise about 0.1 wt. %, 0.2. wt. %, 0.3 wt. %, 0.4 wt. %, 0.5 wt. %, 0.6 wt. %, 0.7 wt. %, 0.8 wt. %, 0.9 wt. %, 1 wt. %, 2 wt. %, 3 wt. %, 4 wt. %, 5 wt. %, 5 wt. %, 7 wt. %, 8 wt. %, 9 wt. %, or about 10 wt. % agar.

In some cases, the critical temperature of the gel composition to form a liquid (e.g., a first state) is greater than about 20° C. In some cases, the critical temperature of the gel composition to form a liquid is greater than about 25° C. In some cases, the critical temperature of the gel composition to form a liquid is greater than about 30° C. In some cases, the critical temperature of the gel composition to form a liquid is greater than about 35° C. In some cases, the critical temperature of the gel composition to form a liquid is greater than about 40° C. In some cases, the critical temperature of the gel composition to form a liquid is greater than about 50° C. In some cases, the critical temperature of the gel composition to form a liquid is greater than about 60° C. In some cases, the critical temperature of the gel composition to form a liquid is greater than about 70° C. In some cases, the critical temperature of the gel composition to form a liquid is greater than about 80° C. Depending on the type of gel-forming compound and the intended use of the gel-forming compound, the critical temperature of the gel composition may vary.

In the liquid form, a biological specimen can be mixed with the gel composition. For example, for a gelling composition that exhibits gel-sol thermo-reversibility, the biological specimen can be mixed with the gel composition in the sol or liquid form. By "thermoreversible" we refer to the property of gel formation a gel composition above or below a critical transition point while a liquid or sol form of the composition exists at temperatures above or below that transition point. Additionally, reagents, such as stains, dyes (fluorescent probes), growth factors, and reporter molecules, can be introduced to generate homogeneous preparations. Recovery of cells or particles from the liquid phase, or from dilutions of the gel, can be achieved by conventional methods including centrifugation methods, filtration or magnetic separation, or combinations thereof.

In some embodiments, the critical temperature of the gel composition to form a gel (e.g., a second state) is less than about 20° C. In some embodiments, the critical temperature of the gel composition to form a gel is less than about 15° C. In some embodiments, the critical temperature of the gel composition to form a gel is less than about 10° C. In some embodiments, the critical temperature of the gel composition to form a gel is less than about 2° C. In some embodiments, the critical temperature of the gel composition to form a gel is less than about 2° C. In the gel form, cells or particles of the immobilized biological specimens are embedded or supported in a three-dimensional gel matrix. The gel matrix can preserve cell function or particle integrity in the matrix. That is, the cells in the biological specimen are not ruptured and remain in intact in the gel matrix. In this gel matrix, cells or particles can be introduced at low temperature preserving cell function or particle integrity without the thermal shock potential of using gels which only become liquid at elevated temperatures. In some embodiments, the gel matrix retains cell viability and cell function for periods of time sufficient for the purposes of analysis.

The gel composition may have optical properties that enable light-based optical analysis of the biological samples. In particular, the gel may have a composition comprising a polymer as a support matrix in the optical analysis of particles. For example, the gel may have low absorbance of light and may be non-fluorescent. In some embodiments, the gel composition may be optically clear, transparent, or both.

The composition of the gel may be suitable for calibration, optical alignment or orientation in methodologies requiring the collection of light. For example, the composition may be used for calibration, point-spread function determination and event orientation within optical slices of two or more dimensions. Advantageously, the support matrix composition forms an addressable array for the purpose of mechanical delivery of analytes and subsequent optical analyses requiring the collection of light. Non-limiting examples include transmission, phase-contrast, fluorescence, fluorescence-lifetime, bioluminescence, chemoluminescence, anisotropy, light scattering, and refractive index or any appropriate combination thereof.

The gel composition be added to a biological specimen at gelling concentrations to provide an over layer for adherent cultures or planar preparations of live or fixed cells. The gel can provide a convenient way to protect cells for in situ staining or labeling of cells, or both. In some cases, the liquid-gel transition of the gel is a function of temperature, and therefore provides a way of spreading the gel at higher temperature and controlling the gel depth by halting spreading through gel formation by decreasing the temperature of the preparation. Additionally, the adherent properties would allow for inversion of a gelled specimen so that inverted microscopy formats can be used. Here, the gel can provide an aqueous-gel phase between the specimen and another optical interface for imaging.

The gel can form a cell- or particle- or reagent-support/embedding matrix based upon the formulation of the gel composition, which provides advantageous properties for manipulation, processing and analysis. At room temperature (above 15° C. selected by formulation to achieve a gel form at room temperature to 37° C.), the gel may be hydrophobic.

In some embodiments, the gel has low cytotoxicity to enable live cell processing. In some cases, the gel composition is substantially non-cytotoxic. For example, with respect to micro-organisms, the gel should have low toxicity in the stable gel form. As used herein, "cytotoxic" refers to the property of causing lethal damage to mammalian cell structure or function. In some embodiments, the pH of the gel formulation is important for cell viability. For example, depending on the biological specimen, the pH of the gel formulation may need to be adjusted to a certain pH range by adding a buffer solution.

Flow Imaging

In some embodiments, the methods for immobilizing a biological specimen described herein can be particularly useful for flow-imaging microscopy. The gel can act as a support matrix to substantially immobilize cells or particles to reduce movement for the purposes of imaging. Additionally, the gel composition can form a high viscosity solution containing the biological specimen to slow the flow of the biological specimen in the flow cytometer to provide an image capture time ranging from 5 seconds to 30 seconds, In this way, the gel formation inhibits the Brownian motion of the cells in the biological sample, while providing a gel solution of sufficient viscosity for flow imaging. Immobilization important to allow for inspection of high density and information-rich fields. Non-limiting examples may include counting of cell/particle subsets marked by different fluorescent dyes or features. For example, immobilizing the biological specimen can allow for inspection of imaging changes in cell/particle features with time, the multiplex analysis of cells/particles that require sequential acquisition, the imaging of asynchronous events in fields of cells/particles, and the high-resolution imaging of sub-cellular events which could be compromised if the cell itself was mobile.

In a flow imaging cytometer, cells in a specimen solution travel in a flow through an image capturing area that is continuously monitored to perform cell photography. In some cases, cells/particles in a biological sample are treated with a fluorescent stain, and the specimen solution is irradiated with light from a pulsed light source for exciting fluorescence, and/or with infrared light f©r monitoring the passage of cells through the cytometer. Then, when a cell particle of interest is detected, the cell particle is irradiated with a light pulse of high luminance to obtain a still picture of the fluorescence-emitting cell. At detection of the cell, a source of light can be actuated to acquire a light-based image of the cell.

Beneficially, the methods described enable the use of flow imaging with new image processing technologies that require extended image-capture times. For example, by adding a gel composition to a biological specimen that is provided to the flow imaging cytometer, the viscosity of the sample fluid can be controlled thereby reducing the movement/speed of analytes in a specimen. This provides an extended period of time for image capture allowing for a large number of low-resolution images. For example, several hundred low-resolution images can be taken of the specimen in its immobilized state. The microscopic imaging devices can take advantage of image processing improvements that post-process the low-resolution images to produce a high-resolution image. Additionally, relatively cheap optics can be used for capturing low-resolution images.

General methodologies can be described which provide for applications in which live or fixed cells, particles or beads can be incorporated into the gel with formulations which may include informative dyes or other reporter molecules. These basic protocols can be adapted for specific applications in candidate product screening in drug discovery, cell- and particle/bead-based biotechnologies and numerous applications in imaging and microscopy and non-imaging plate based assays.

Wet Mount

In some embodiments, the method of immobilizing a biological specimen can be used for wet-mount microscopy. An aliquot of the gel matrix comprising the immobilized biological specimen can be suspended between a slide and a coverslip. To prepare a wet mount, a sample of the specimen is placed into a test tube to which an aliquot of the desired lyse or stain composition is added and a gel composition is added. The specimen is mixed well and capped and incubated at room temperature to allow the lyse or stains to penetrate the sample. In some cases, incubation with the lyse or stain may proceed for 12 to 18 hours. A thin drop of the specimen is placed on a microscope slide and covered with a microscope coverslip. The wet mount is then analyzed in a hemocytometer.

In wet-mount microscopy, specimens are typically provided in liquid form so Brownian motion is a problem. Brownian motion causes enough mobility in the cell that taking hundreds of low resolution images for the new imaging techniques does not work because the motion of the cell is too high to capture a good quality image. For example, U.S. Patent Publication No. 2013/0169948, the contents of which is incorporated by reference in s entirety for all intents and purposes, describes a process of taking a plurality of images of different resolutions to produce a high-resolution image. By adding the gel composition to the specimen solution, the specimen can be immobilized for image capture. For example, a specimen can be positioned in the liquid phase of the gel and held in place until polymerization of the liquid phase produces sufficient gel strength to immobilize the specimen.

The thin drop of biological specimen can be prepared according to the methods described herein to immobilize the biological specimen. For example, a biological specimen can be added to a gel composition at a temperature above the critical temperature of the gel composition to form an aqueous mixture. An aliquot of the desired lyse or stain composition can be added to the aqueous mixture and incubated for a period of time. The temperature of the aqueous composition can be reduced below the critical temperature of the gel composition to form a gel matrix containing the biological specimen. A sample of the gel matrix containing the biological specimen can placed on a microscope slide. In some embodiments, the microscope slide can be covered with a microscope coverslip. Using the formed gel matrix, a slide with whole, intact cells for wet mount microscopy is produced, and movement of the cells is inhibited. In this case, multiple low-resolution images can be captured while the cells are immobilized. Then, an image-processing technique is applied to convert the multiple low-resolution images into a high-resolution image.

In some cases, the specimen can be stained in a liquid phase of the gel. For example, temperature of the specimen solution can be raised above the critical temperature of the gel to form a liquid, a stain can be added to specimen solution, and then the temperature of specimen solution can be lowered below the critical point to form a gel.

The surface area of the imaging substrate can affect hardening of the specimen solution comprising the biological specimen. For example, depositing a small quantity of specimen solution on an imaging substrate with a large surface area can cause the specimen solution to harden upon contact. In some cases, depositing a specimen solution on an imaging substrate with a large surface area (e.g., a flat bottom plate) may cause the sample to harden before the specimen solution can be spread into a thin layer on the imaging substrate resulting in poor image quality.

In some embodiments, the specimen solution can be deposited on an imaging substrate having a surface area that enables the sample solution to be spread on the imaging substrate before hardening. For example, a specific quantity of the specimen solution can be deposited onto an imaging substrate (e.g., a microscope slide) to have a specific ratio of the volume of specimen solution to the surface area of the imaging substrate. It is contemplated that the ratio of the volume of the specimen solution to the surface area of the imaging substrate can be controlled to prevent hardening upon contact with the imaging substrate. For example, the ratio of the volume of the specimen solution to the surface area of the imaging substrate can range from 0.001:1 to 20:1, e.g., from 0.01:1 to 15:1, from 0.05:1 to 10:1, from 0.1:1 to 8:1, from 0.5:1 to 6:1, from 0.8:1 to 4:1, from 1:1 to 3:1. By controlling this ratio, the specimen solution can be spread into a thin layer on the imaging substrate for a larger field of view during imaging.

In some embodiments, the methods described herein can be utilized in an automated system. For example, a gel composition can be provided in or on an imaging substrate including, for example, multichamber plate, a reel, or strip, comprising a series of pockets. A biological sample and, optionally, a reagent (e.g., a stain or lyse) can be added to the pocket containing the gel composition. For example, a stain or lyse can be added to the pocket containing the gel composition. Once staining or lysing is complete, the pockets are cooled causing the reaction mixture to gelate, thereby immobilizing the cells/particle in the gel matrix. The cells/particle in the gel matrix can then be imaged using the earlier described imaging techniques that require long exposure time or multiple exposures without the subject moving. After imaging, the reaction mixture can be heated to transition the gel matrix to a liquid form and discarded as waste.

Figure 2:
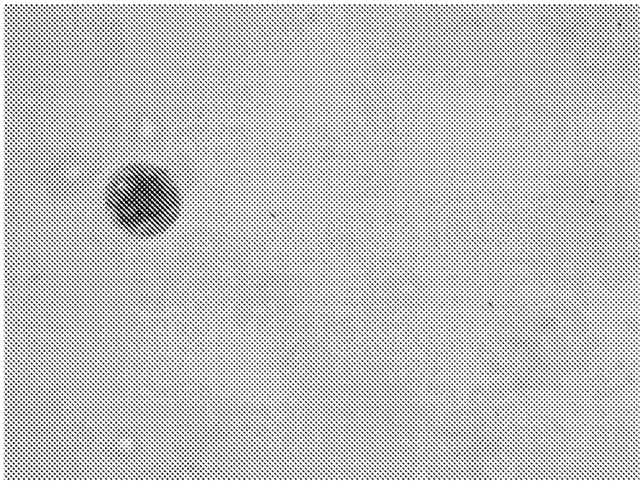
FIG. 2 shows an example of an immobilized eosinophil in a gel according to one embodiment of the present disclosure.
Figure 3:
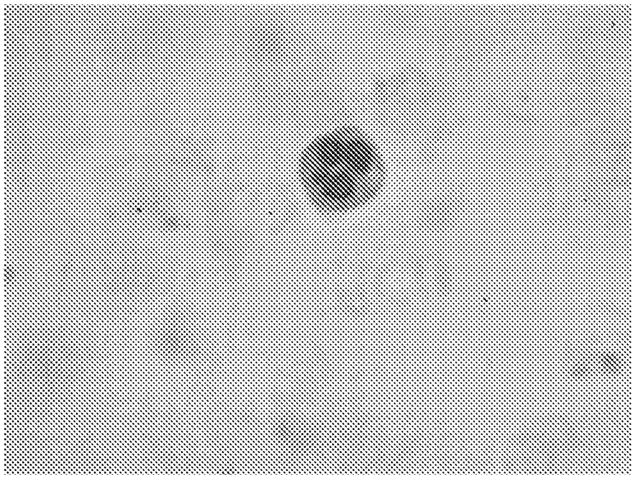
FIG. 3 shows an example of an immobilized neutrophil in a gel according to one embodiment of the present disclosure.
Figure 4:
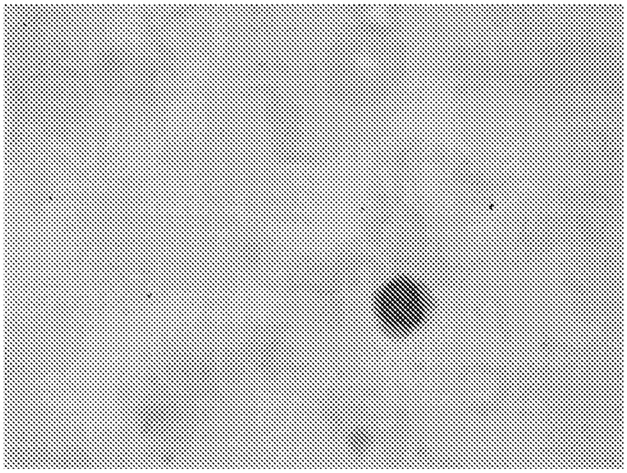
FIG. 4 shows an example of an immobilized lymphocyte in a gel according to one embodiment of the present disclosure.
Figure 5:
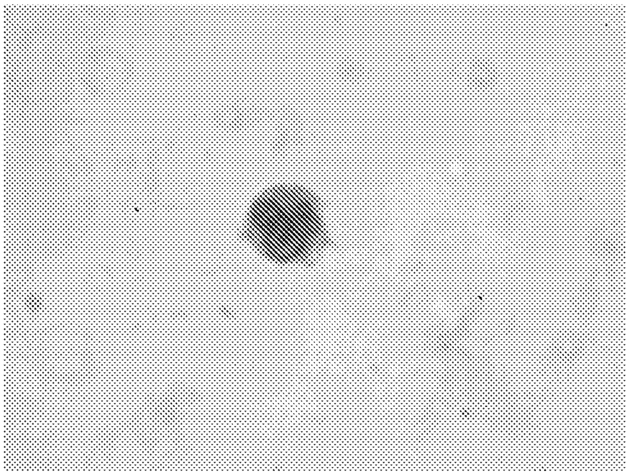
FIG. 5 shows an example of an immobilized monocyte in a gel according to one embodiment of the present disclosure.

FIGS. 1-5 show images of specific immobilized cells from a biological specimen in a gel according embodiments of the present disclosure. In these examples, the biological specimen was mixed with a stain and incubated at 47° C. for about 45 seconds. A liquid agar gel composition was then added to the stained biological specimen to form a sample solution. The sample solution was placed on a microscope slide and allowed to cool to room temperature. At room temperature, the liquid agar gel composition formed a gel to immobilize the cells in the sample solution. The prepared microscope slide was viewed under a standard microscope from Olympus (Lake Success, N.Y.) and pictures were taken using a camera attached to the microscope. Each of the images in FIGS. 1-5 show cells from the biological specimen that were immobilized in the gel (e.g., hardened gel). Specifically, FIG. 1 shows an example of an immobilized basophil, FIG. 2 shows an example of an immobilized eosinophil, FIG. 3 shows an example of an immobilized neutrophil, FIG. 4 shows an example of an immobilized lymphocyte, and FIG. 5 shows an example of an immobilized monocyte

EXAMPLES

Gel imaging experiments were conducted on biological samples immobilized in a formulation comprised of a gelling agent, Agar powder from Sigma Aldrich Co. Ltd and deionized water. The Agar powder was the gelling component.

Comparative Examples 1-3 each comprised a formulation comprised of Agar A-7002 (from Sigma Aldrich Co. Ltd) and deionized water. Agar A-7002 has a melting point greater than 75° C.

For Comparative Example 1, Agar A-7002 powder was mixed with deionized water in a flask to form a 10 wt. % Agar solution. The flask containing the 10 wt. % Agar solution was placed in a 75° C. hot water bath, The Agar A-7002 powder did not completely dissolve in the hot water bath. The temperature of the hot water bath was raised to 80° C., however, the Agar A-7002 powder still did not dissolve.

For Comparative Example 2, Agar A-7002 powder was mixed with deionized water in a flask to form a 5 wt. % Agar solution. The flask containing the 5 wt. % Agar solution was placed in a 80° C. hot water bath. The Agar A-7002 powder dissolved in the 5 wt. % Agar solution, however, the solution was too viscous. Therefore, the 5 wt. % Agar solution was difficult to pipet and had to be discarded.

In Comparative Example 3, Agar A-7002 powder was mixed with deionized water in a flask to form a 1 wt. % Agar solution. The flask containing the 1 wt. % Agar solution was placed in a 80° C. hot water bath. The Agar A-7002 powder dissolved in the 1 wt. % Agar solution, however, the 1 wt. % Agar solution was difficult to pipet because of the temperature change from 80° C. to room temperature. Therefore, the 1 wt. % Agar solution comprised of Agar A-7002 was also impractical to use and had to be discarded.

Comparative Examples 4 and 5 each comprised a formulation comprised of low melting point agar powder mixed with deionized water. Comparative Example 4 comprised a formulation including Agar A-9414 (from Sigma Aldrich Co. Ltd) powder which has a melting point less than 60° C. Comparative Example 5 comprised a formulation that comprised Agar A-9045 (from Sigma Aldrich Co. Ltd) powder which has a melting point less than or equal to 65° C.

For Comparative Example 4, Agar A-9414 powder was mixed with deionized water in a flask to form a 1 wt. % Agar solution. The flask containing the 1 wt. % Agar solution was placed in a 65° C. hot water bath. The Agar A-9414 powder dissolved in the 1 wt. % Agar solution in the hot water bath.

For Comparative Example 5, Agar A-9045 powder was mixed with deionized water in a flask to form a 1 wt. % Agar solution. The flask containing the 1 wt. % Agar solution was placed in a 65° C. hot water bath. The Agar A-9045 powder dissolved in the 1 wt. % Agar solution in the hot water bath.

For each of Comparative Examples 4 and 5, 100 μl of the dissolved agar solutions were mixed with a stained biological sample (e.g., biological sample diluted in stain at a ratio of 1:5). The mixed patient samples were poured into a six-well flat bottom culture plate at room temperature. Each of the agar solutions of Comparative Examples 4 and 5 became gelatinous upon contact with the plate and did not allow for the mixed patient sample to be spread into a thin layer on the well. Consequently, the large surface area of the well (34.8 mm diameter) with the small volume of patient sample (350 μl) at room temperature was not successful with either agar solution. Although the low-melting point agar powders dissolved in solution for these examples, the large surface area of the imaging substrate caused the patient sample to solidify before it could be spread into a thin layer.

Example 1 was prepared by mixing Agar A-9045 powder with deionized water to form a 5 wt. % Agar solution. The 5 wt. % Agar solution was placed in a 65° C. water bath and the Agar A-9045 powder completely dissolved in the solution. 50-75 μl of the 5 wt. % Agar solution was mixed with a stained patient sample (e.g., biological sample diluted in stain at a ratio of 1:5). The mixed patient samples were pipetted onto a two-well microscope slide. The mixed patient samples hardened in the wells in about 15 to 20 seconds which allowed the mixed patient samples to be spread into a thin layer before hardening. The slide was placed under a microscope which surprisingly showed that the Brownian movement of the cells normally seen one a conventional slide was not present due to gel formation. Additionally, the patient sample (e.g., the cells) itself was intact and did not show signs of being broken or destroyed. Beneficially, the ratio of the volume of the mixed patient sample to the surface area of the imaging substrate was sufficient to allow the mixed patient samples to be spread into a thin layer before hardening.

It should be understood that various different features described herein may be used interchangeably with various embodiments. For example, if one feature is described with respect to particular example, it is understood that that same feature may be used with other examples as well.

Although certain embodiments have been shown and described, it should be understood that changes and modifications, additions and deletions may be made to the structures and methods recited above and shown in the drawings without departing from the scope or spirit of the disclosure or the following claims.

What is claimed is:

1. A method for immobilizing a biological specimen for microscopic imaging, comprising:

providing a gel composition in a first state that is a liquid, wherein the gel composition is thermally reversible between the first state and a second state at a critical temperature, wherein the critical temperature is from about 15° C. to about 25° C., wherein the gel composition is a liquid above the critical temperature and a gel below the critical temperature;

adding a biological specimen to the gel composition to form an aqueous mixture;

adding a reagent to the aqueous mixture when the gel composition is in the first state, wherein the reagent comprises a lysing agent;

spreading the liquid aqueous mixture into a layer on a surface of an imaging substrate, wherein the surface of the imaging substrate is below the critical temperature, and wherein a ratio of a volume of the liquid aqueous mixture spread on the imaging substrate to an area of the surface of the imaging substrate is sufficiently large to avoid hardening of the liquid aqueous mixture to a gel matrix before it has been spread into a layer and is larger than a corresponding ratio that results in hardening of the liquid aqueous mixture to the gel matrix before it has been spread into the layer;

cooling the spread liquid aqueous mixture below the critical temperature of the gel composition to the second state to harden the gel composition and to form the gel matrix, wherein the gel matrix is a transparent gel matrix, and wherein the biological specimen is immobilized in the gel matrix; and capturing a plurality of images of the biological specimen in the gel matrix.

2. The method of claim 1, wherein the reagent comprises a stain, the method further comprising:

adding the stain to the aqueous mixture when the gel composition is in the first state.

3. The method of claim 1, wherein the biological specimen comprises live cells.

4. The method of claim 1, wherein the gel composition comprises alginate, carrageenan, beta-carrageenan, agar, agarose, curdlan, pullulan, gellan, furcellaran, beta-carrageenan, beta-1,3-glucans, gelatin, polyoxyalkylene containing compounds, or any combination thereof.

5. The method of claim 1, wherein the gel matrix serves as a support for analysis of the biological specimen by flow imaging, microscopy or non-imaging plate-based assays.

6. The method of claim 1, further comprising:

preparing a specimen sample, wherein preparing the specimen sample includes providing the gel composition, adding the biological specimen to the gel composition, and cooling the aqueous mixture to from the gel matrix.

7. The method of claim 6, further comprising:

flowing the specimen sample through an image capture area of a flow imaging cytometer.

8. The method of claim 7, wherein the flow cytometer captures a plurality of low resolution images of the specimen sample.

9. The method of claim 7, wherein portions of the specimen sample are exposed to the image capture area for at least 5 seconds.

10. The method of claim 6, further comprising:

placing a portion of the specimen sample on a microscope slide.

11. The method of claim 1, wherein the gel composition is a liquid at temperatures of greater than 40° C.

12. The method of claim 1, wherein the gel composition is a liquid at temperatures of greater than 50° C.

13. The method of claim 1, wherein the gel composition comprises agar powder having a melting point of less than about 75° C.

14. A method for immobilizing a biological specimen for microscopic imaging, comprising:

providing a gel composition in a first state that is a liquid, wherein the gel composition is thermally reversible between the first state and a second state at a critical temperature, wherein the gel composition is a liquid at temperatures of greater than 40° C.;

adding a biological specimen to the gel composition to form an aqueous mixture;

adding a reagent to the aqueous mixture when the gel composition is in the first state. wherein the reagent comprises a lysing agent;

spreading the liquid aqueous mixture into a layer on a surface of an imaging substrate, wherein the surface of the imaging substrate is below the critical temperature, and wherein a ratio of a volume of the liquid aqueous mixture spread on the imaging substrate to an area of the surface of the imaging substrate is sufficiently large to avoid hardening of the liquid aqueous mixture to a gel matrix before it has been spread into a layer and is larger than a corresponding ratio that results in hardening of the liquid aqueous mixture to the gel matrix before it has been spread into the layer;

cooling the spread liquid aqueous mixture below the critical temperature of the gel composition to the second state to form the gel matrix, wherein the gel matrix is a transparent gel matrix, and wherein the biological specimen is immobilized in the gel matrix; and capturing a plurality of images of the biological specimen in the gel matrix.

15. The method of claim 14, wherein the gel composition is a liquid at temperatures greater than 50° C.

16. A method for immobilizing a biological specimen for microscopic imaging, comprising:

providing a gel composition in a first state that is a liquid, wherein the gel composition is thermally reversible between the first state and a second state at a critical temperature, wherein the critical temperature of the gel composition is greater than 40° C.;

adding a biological specimen to the gel composition to form an aqueous mixture;

adding a reagent to the aqueous mixture when the gel composition is in the first state, wherein the reagent comprises a lysing agent;

spreading liquid aqueous mixture into a layer on a surface of an imaging substrate, wherein the surface of the imaging substrate is below the critical temperature, and wherein a ratio of a volume of the liquid aqueous mixture spread on the imaging substrate to an area of the surface of the imaging substrate is sufficiently large to avoid hardening of the liquid aqueous mixture to a gel matrix before it has been spread into a layer and is larger than a corresponding ratio that results in hardening of the liquid aqueous mixture to the gel matrix before it has been spread into the layer;

cooling the spread liquid aqueous mixture below the critical temperature of the gel composition to the second state to form the gel matrix, wherein the gel matrix is a transparent gel matrix, and wherein the biological specimen is immobilized in the gel matrix; and capturing a plurality of images of the biological specimen in the gel matrix.

17. The method of claim 16, wherein the critical temperature of the gel composition is greater than 50° C.

* * * * *